United States Patent [19]

Che

[11] Patent Number: 4,642,394

[45] Date of Patent: Feb. 10, 1987

[54] PRODUCTION OF PROPANEDIOLS

[75] Inventor: Tessie M. Che, Westfield, N.J.

[73] Assignee: Celanese Corporation, New York, N.Y.

[21] Appl. No.: 755,633

[22] Filed: Jul. 16, 1985

[51] Int. Cl.$^4$ .................. C07C 29/132; C07C 29/60; C07C 31/20

[52] U.S. Cl. .................................................. 568/861

[58] Field of Search ........................................ 568/861

[56] References Cited

U.S. PATENT DOCUMENTS 1,963,997  6/1934  Larchar ................................ 568/861

4,401,823  8/1983  Arena .................................. 568/861
4,496,780  1/1985  Arena .................................. 568/861

FOREIGN PATENT DOCUMENTS 0149905  12/1978  Japan .................................. 568/861
490211  8/1938  United Kingdom ................ 568/861

*Primary Examiner*—J. E. Evans
*Attorney, Agent, or Firm*—Depaoli & O'Brien

[57] ABSTRACT

This invention provides a process for the production of propanediols by reaction of glycerol and synthesis gas in a basic organic solvent in the presence of a tungsten and Group VIII metal-containing catalyst composition.

15 Claims, No Drawings

PRODUCTION OF PROPANEDIOLS

BACKGROUND OF THE INVENTION

The conversion of carbohydrates to glycerol and other short chain polyols generally is accomplished in two stages. In the first stage a carbohydrate such as hexose is hydrogenate to produce a polyol without hydrogenolysis of the starting material carbon structure. In the second stage the polyol is subjected to hydrogenolysis conditions to produce polyols of shorter chain length.

U.S. Pat. Nos. 1,963,999; 3,935,284; and 4,380,679 describe catalytic systems for converting saccharides such as starch, glucose and fructose to hexitols such as sorbitol and mannitol.

U.S. Pat. Nos. 1,963,997; 2,335,731; 2,852,570;and 4,404,411 describe processes which utilize hydrogenolysis conditions to convert hexitols to lower polyols such as glycerol, propylene glycol and ethylene glycol.

U.S. Pat. Nos. 2,004,135; 2,209,055; 4,380,678; and 4,476,331 describe two-stage processes for hydrogenation and hydrogenolysis of carbohydrates to lower polyols such as glycerol and $C_2$-$C_3$ glycols.

U.S. Pat. No. 3,965,199 describes a one-step process for converting a carbohydrate by hydrogenation and hydrogenolysis to glycerol and glycol products in the presence of a catalyst consisting of finely divided metallic nickel and tungsten oxide on a carrier.

There is continuing interest in the development of new and improved processes for efficient conversion of higher polyhydric starting materials selectively to lower polyhydric products.

Accordingly, it is an object of this invention to provide a process for converting a higher polyhydric hydrocarbon to a lower polyhydric hydrocarbon.

It is another object of this invention to provide a process for converting glycerol selectively to propanediols in a homogeneous catalytic reaction medium.

Other objects and advantages of the present invention shall become apparent from the accompanying description and examples.

DESCRIPTION OF THE INVENTION

One or more objects of the present invention are accomplished by the provision of a process for the conversion of glycerol to lower oxygenated hydrocarbons which comprises reacting glycerol, carbon monoxide and hydrogen in a basic organic solvent medium in contact with a soluble catalyst composition containing tungsten and Group VIII metal components, to yield a product mixture comprising propanediols.

In another embodiment this invention provides a process for the production of propanediol which comprises reacting glycerol, carbon monoxide and hydrogen in an aprotic organic amide solvent medium in the presence of a soluble catalyst composition containing tungsten and Group VIII metal compounds, at a temperature between about 100°–200° C. and a pressure between about 500–10,000 psi to yield a product mixture comprising 1,2-propanediol and 1,3-propanediol.

The term "basic organic solvent" refers to a liquid organic medium which is at least weakly alkaline in reactivity relative to a strong acid. Illustrative of basic organic solvents are amines and amides which have the following base strengths in terms of pKa relative to ammonia (pKa=33), e.g., pyrrolidine (11.3), ethylamine (10.8), diethylamine (11.1), triethylamine (10.8), benzylamine (9.5), morpholine (8.3), pyridine (5.2), aniline (4.6), N-methylacetamide (−0.46), acetamide (−0.63), 2-pyrrolidinone (−0.65), 1-methyl-2-pyrrolidinone (−0.75) and benzamide (−1.5).

The process can be conducted by charging a reactor with solvent medium, glycerol and catalyst, and pressuring the reaction system with synthesis gas.

The carbon monoxide/hydrogen gas mixture can be employed in a molar ratio between about 1:10–10:1 of carbon monoxide to hydrogen, with the preferred molar ratio being between about 1:2–2:1 of carbon monoxide to hydrogen. An inert diluent gas such as nitrogen can be included in the pressure system.

The basic organic solvent is employed in a sufficient quantity to provide a liquid phase reaction medium in the reactor. A typical volume of basic organic solvent will range between about 5–100 milliliters per gram of glycerol in the reaction medium.

The catalyst composition can be employed in a quantity between about 0.001–1.0 gram-atom of tungsten and Group VIII metals per liter of reaction medium. Typically between about 0.005–0.1 gram-atom of active metal content in the catalyst composition is utilized per liter of reaction medium. With reference to the glycerol starting material, the catalyst composition usually is employed in a quantity between about 0.5–20 weight percent, based on the weight of glycerol.

The invention process is conducted at a temperature between about 75°–250° C., and usually will be in the range between about 100°–200° C.

The pressure employed in the reaction system can range between about 100–15,000 psi. The synthesis gas partial pressure on the average will be in the range between about 200–10,000 psi.

The process is conducted for a reaction period between about 1.0–30 hours, and typically will be in the range of about 1–5 hours.

The organic solvent employed in the process generally is a polar medium which is at least weakly alkaline with respect to the ability to form salts with strongly acidic compounds.

Illustrative of suitable basic organic solvents are methylamine, dimethylamine, trimethylamine, ethylamine, diethylamine, triethylamine, triethanolamine, tri(-chloromethyl)amine, pyridine, piperidine, piperazine, and the like.

A preferred type of basic organic solvent is an aprotic organic amide. Illustrative of this type of solvent are N,N-dimethylformamide, N,N-dimethylacetamide, 1-methyl-2-pyrrolidinone, 1-methyl-2-piperidone, hexamethylphosphoric triamide, 1,1,3,3-tetramethylurea, and the like.

The basic organic solvent can be employed in admixture with other solvent media such as water, methanol, ethanol, tetrahydrofuran, diethyl ether, acetonitrile, benzonitrile, dioxane, ethylene glycol alkyl ether, ethyl acetate, butyrolactone, and the like.

Operation of the invention process appears to require a "basic" reaction medium in order to achieve a desirable rate of reaction and yield of propanediol products. This requirement is satisfied by the use of a basic organic solvent.

Alternatively, the required reaction medium basicity can be provided by employing an inorganic base such as a metal hydroxide or metal carbonate, or a quaternary ammonium compound such as tetramethylammonium hydroxide, in combination with a polar solvent medium such as aqueous methanol.

The basic reaction medium tends to stabilize the catalyst and maintain the reactivity of the catalyst under the invention process hydrogenation conditions.

For purposes of the present invention process, an essential parameter for the production of propanediols is the presence of a homogeneous catalyst system which contains active tungsten and Group VIII metal constituents.

The presence of tungsten metal is critical for obtaining efficient production of propanediol products. Optimal results are achieved when the tungsten metal is employed in combination with a Group VIII metal such as iron, cobalt, nickel, ruthenium, rhodium, palladium, osmium or platinum. Additional metal components may be included as promoters in the tungsten/Group VIII metal combination, e.g., metals such as titanium, zirconium, tin, and the like.

The gram-atom ratio of tungsten metal component to Group VIII metal component in the catalyst composition can be varied in the range between about 1–10:1 of tungsten to Group VIII metal.

The tungsten and Group VIII metals can be incorporated in the catalyst system in any convenient form of chemical compounds. Illustrative of suitable compounds are tungsten and Group VIII metal oxides, acetylacetonates, sulfates, tetrafluoroborates, formates, acetates, propionates, oxalates, gluconates, lactates, citrates, cyclopentadienides, and the like. Illustrative of metal compound species are tungstic acid, cobalt carbonyl, and rhodium carbonyl acetylacetonate.

The tungsten and Group VIII metal compounds initially need not be soluble in the reaction medium. Solubilization to a homogeneous reaction medium is effected or completed by contact with synthesis gas under the reaction conditions. A homogeneous catalyst system is an essential feature of the invention process.

The presence of carbon monoxide contributes to the solubilization and stabilization and activation of the catalyst species. Without the presence of carbon monoxide, the conversion of glycerol to propanediol proceeds less efficiently.

After the completion of a process run, the propanediols can be separated and recovered by conventional means such as distillation. The catalyst composition can be isolated and recycled in the process.

The following examples are further illustrative of the present invention. The components and specific ingredients are presented as being typical, and various modifications can be derived in view of the foregoing disclosure within the scope of the invention.

EXAMPLE I

This Example illustrates a process embodiment in accordance with the present invention.

A 300 cc Hastelloy C autoclave equipped with a Magnedrive mechanical stirrer is charged with 0.15 g (0.58 mmole) of Rh(CO)$_2$ acetylacetonate, 1 g (4 mmole) of H$_2$WO$_4$ and 20 g (217 mmole) of glycerol in 50 g of 1-methyl-2-pyrrolidinone solvent. The reactor is heated to 200° C. and maintained at 4600 psig of 1:2 (CO:H$_2$) synthesis gas. After 24 hours under these conditions, the autoclave is cooled to room temperature and the gas is vented.

Gas chromatographic/mass spectroscopic analysis of the resulting solution indicates product yields of 3.47 g of 1,3-propanediol, 3.83 g of 1,2-propanediol and 0.47 g of 1-propanol.

When a ruthenium, palladium, nickel or cobalt metal component is employed in place of rhodium with the tungsten compound, similar product yield results are obtained.

When a titanium or molybdenum metal promoter component is used with a Group VIII metal and tungsten metal in the catalyst, similar product yield results are obtained.

EXAMPLE II

The Example I procedure is repeated, except that 0.15 g (0.58 mmole) of Rh(CO)$_2$ acetylacetonate alone without a tungsten component is employed as a catalyst. The resulting product mixture contains 0.17 g of 1,3-propanediol, 0.31 g of 1,2-propanediol and 0.05 g of 1-propanol.

The Example I procedure is repeated, except that 2 g (8 mmole) of H$_2$WO$_4$ is employed as the catalyst. The resulting product mixture contains 1.08 g of 1,3-propanediol and 1.02 g of 1,2-propanediol. No formation of 1-propanol product is evident.

The Example I procedure is repeated, except that Rh(CO)$_2$ acetylacetonate is employed with sulfuric acid as the catalyst system. Under these conditions none of the glycerol starting material is converted to propanediol and/or propanol products.

EXAMPLE III

The Example I procedure is repeated, except that hydrogen alone is employed in place of 1:2 (CO:H$_2$) synthesis gas.

The resulting product mixture contains 2.15 g of gas. 1,3-propanediol, 3.24 g of 1,2-propanediol and 2.71 g of 1-propanol.

EXAMPLE IV

The Example I procedure is repeated, except that gamma-butyrolactone is utilized as the solvent medium in place of 1-methyl-2-pyrrolidinone.

The resultant product mixture contains 1.38 g of 1,3-propanediol, 0.15 g of 1,2-propanediol and 10.63 g of 1-propanol.

What is claimed is:

1. A process for the conversion of glycerol to lower oxygenated hydrocarbons which comprises reacting glycerol, carbon monoxide and hydrogen in a basic organic solvent medium in contact with a soluble catalyst composition containing tungsten and Group VIII metal components, to yield a product mixture comprising propanediols.

2. A process in accordance with claim 1 wherein the reaction is conducted at a temperature between 75°–250° C. and a pressure between about 1000–15,000 psi for a reaction period between about 1.0–30 hours.

3. A process in accordance with claim 1 wherein the carbon monoxide and hydrogen are employed in a molar ratio between 1:2–2:1 of carbon monoxide to hydrogen.

4. A process in accordance with claim 1 wherein the basic organic solvent medium comprises an organic amine or amide.

5. A process in accordance with claim 1 wherein the catalyst composition contains tungsten and rhodium metal components.

6. A process in accordance with claim 1 wherein the catalyst composition contains tungsten and cobalt metal components.

7. A process in accordance with claim 1 wherein the catalyst composition contains tungsten, rhodium and titanium metal components.

8. A process for the production of propanediol which comprises reacting glycerol, carbon monoxide and hydrogen in an aprotic organic amide solvent medium in contact with a soluble catalyst composition containing tungsten and Group VIII metal compounds, at a temperature between about 100°–200° C. and a pressure between about 500–10,000 psi to yield a product mixture comprising 1,2-propanediol and 1,3-propanediol.

9. A process in accordance with claim 8 wherein the solvent medium is 1-methyl-2-pyrrolidinone.

10. A process in accordance with claim 8 wherein the solvent medium is 1-methyl-2-piperidone.

11. A process in accordance with claim 8 wherein the catalyst composition contains tungsten and rhodium metal components.

12. A process in accordance with claim 8 wherein the catalyst composition contains tungsten and cobalt metal components.

13. A process in accordance with claim 8 wherein the catalyst composition contains tungsten, rhodium and titanium components.

14. A process in accordance with claim 8 wherein the catalyst composition is a salt of a tungsten and rhodium metal-containing anion and a quaternary ammonium cation.

15. A process in accordance with claim 8 wherein the product mixture contains n-propanol.

* * * * *